United States Patent [19]
Kossmann et al.

[11] Patent Number: 6,001,628
[45] Date of Patent: Dec. 14, 1999

[54] DEBRANCHING ENZYMES AND DNA SEQUENCES CODING THEM, SUITABLE FOR CHANGING THE DEGREE OF BRANCHING OF AMYLOPECTIN STARCH IN PLANTS

[75] Inventors: Jens Kossmann; Michael Emmermann, both of Berlin, Germany; Ivar Virgin, Stockholm, Sweden

[73] Assignee: Hoechst Schering AgrEvo GmbH, Berlin, Germany

[21] Appl. No.: 08/596,257

[22] PCT Filed: Aug. 8, 1994

[86] PCT No.: PCT/EP94/02623

§ 371 Date: Apr. 18, 1996

§ 102(e) Date: Apr. 18, 1996

[87] PCT Pub. No.: WO95/04826

PCT Pub. Date: Feb. 16, 1995

[30]     Foreign Application Priority Data

Aug. 9, 1993 [DE] Germany .............. 43 27 165

[51] Int. Cl.⁶ .............. C12N 9/44; C12N 1/20; C12N 15/00; C07H 21/04
[52] U.S. Cl. .............. 435/210; 435/7.6; 435/69.1; 435/200; 435/252.3; 435/320.1; 536/23.2; 536/23.6; 800/205
[58] Field of Search .............. 435/210, 200, 435/252.3, 320.1, 7.6; 536/23.2, 23.6; 800/205

[56]     References Cited

U.S. PATENT DOCUMENTS

4,454,161   6/1984   Okada .............. 426/48
4,886,678   12/1989   Chiu .............. 426/578

FOREIGN PATENT DOCUMENTS

0479359   4/1992   European Pat. Off. .
05029894  3/1993   European Pat. Off. .
9211382   7/1992   WIPO .
9214827   9/1992   WIPO .

OTHER PUBLICATIONS

Suggs et al. PNAS 78(11), 6613–17, 1981.
Plant Physiology vol. 100, 1992, pp. 1083–1086 Shewmaker, C.K., et al. 'Modifying starch biosynthesis with transgenes in potatoes' see p. 1085, left column, last paragraph.
Agric Biol. Chem., vol. 47, No. 4, 1983, pp. 771–779 Ishizaki, Y., et al. 'Debranching enzymes of potato tubers (Solanum tuberosum L.). I. Purification and some properties of potato isoamylase' cited in the application, see the whole document.
Chemical Abstracts, vol. 99, No. 9, 1983, Columbus, Ohio, US: abstract No. 66467 Ishizaki, Y., et al. Debranching enzymes of potato tubers (solanum tuberosum L.).
II. Purification of a pullulanase (R–enzyme) from potato tubers and comparison of its properties with those of the potato isoamylase see abstract & Denpun Kagaku, vol. 30, No. 1, 1983, pp. 19–29.
J. Bacteriology, vol. 169, No. 5, May 1987 pp. 2301–2306 Katsuragi, N., et al. 'Entire nucleotide sequence of pullulanase gene of Klebsiella aerogenes W70' see figure 2.

*Primary Examiner*—Ponnathapura Achutamurthy
*Assistant Examiner*—Tekchand Saidha
*Attorney, Agent, or Firm*—Frommer Lawrence & Haug LLP

[57]                ABSTRACT

DNA sequences are described which on the codogenic strand code plant debranching enzymes, whose transcripts formed in transgenic plants code new proteins with the enzymatic activity of debranching enzymes which in transgenic plants reduce the degree of branching of amylopectin starch and DNA sequences which on the codogenic strand code plant debranching enzymes, whose transcripts formed in transgenic plants prevent the synthesis of proteins with the enzymatic activity of debranching enzymes, which in the transgenic plants increases the degree of branching of amylopectin starch, as well as plasmids on which these DNA sequences are localized, which can be introduced into plant cells and plants. Also described is a process for the production of plants changed by genetic engineering whose amylopectin starch is modified, and the modified starch obtainable from these plants.

17 Claims, 2 Drawing Sheets

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 21 amino acids
      (B) TYPE: amino acid
      (C) STRANDEDNESS:
      (D) TOPOLOGY: linear    (ii) MOLECULE TYPE: peptide    (xi) SEQUENCE DESCRIPTION: SEQ ID NO:1:

Arg Thr Leu Leu Val Asn Leu Asp Ser Asp Asp Val Lys Pro Glu Gly
1               5                   10                  15

Gly Asp Asn Leu Gln
            20

(2) INFORMATION FOR SEQ ID NO:2:

(i) SEQUENCE CHARACTERISTICS:
      (A) LENGTH: 20 amino acids
      (B) TYPE: amino acid
      (C) STRANDEDNESS:
      (D) TOPOLOGY: linear    (ii) MOLECULE TYPE: peptide    (vi) ORIGINAL SOURCE:
      (A) ORGANISM: solanum tuberosum    (xi) SEQUENCE DESCRIPTION: SEQ ID NO:2:

```
Arg Leu Ser Ser Ala Gly Ile Thr His Val His Leu Leu Pro Thr Tyr
1               5                   10                  15

Gln Phe Ala Gly
            20
```

(2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS:
        (D) TOPOLOGY: linear     (ii) MOLECULE TYPE: peptide     (vi) ORIGINAL SOURCE:
        (A) ORGANISM: solanum tuberosum     (xi) SEQUENCE DESCRIPTION: SEQ ID NO:3:

```
Gly Ser Glu Val Leu Met His Asp Gly Lys
1               5                   10
```

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS:
        (D) TOPOLOGY: linear     (ii) MOLECULE TYPE: peptide     (vi) ORIGINAL SOURCE:
        (A) ORGANISM: solanum tuberosum     (xi) SEQUENCE DESCRIPTION: SEQ ID NO:4:

```
Ser Pro Ser Glu Ala Asp Pro Val Glu Ile Val Gln Leu Lys
1               5                   10
```

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS:
        (D) TOPOLOGY: linear     (ii) MOLECULE TYPE: peptide     (vi) ORIGINAL SOURCE:
        (A) ORGANISM: solanum tuberosum     (xi) SEQUENCE DESCRIPTION: SEQ ID NO:5:

```
Asp Cys Ile Gln Val Gly Met Ala Ala Asn Asp Lys
1               5                   10
```

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS:
        (D) TOPOLOGY: linear     (ii) MOLECULE TYPE: peptide     (vi) ORIGINAL SOURCE:
        (A) ORGANISM: solanum tuberosum     (xi) SEQUENCE DESCRIPTION: SEQ ID NO:6:

Lys Leu Gln Leu His Pro Val Gln Met Asn

```
1               5               10
```

(2) INFORMATION FOR SEQ ID NO:7:

(i) SEQUENCE CHARACTERISTICS:
        (A) LENGTH: 10 amino acids
        (B) TYPE: amino acid
        (C) STRANDEDNESS:
        (D) TOPOLOGY: linear     (ii) MOLECULE TYPE: peptide     (vi) ORIGINAL SOURCE:
        (A) ORGANISM: solanum tuberosum     (xi) SEQUENCE DESCRIPTION: SEQ ID NO:7:

```
Glu Leu Asp Gly Val Val Trp Ser Ala Glu
1               5                   10
```

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS:
        (D) TOPOLOGY: linear     (ii) MOLECULE TYPE: peptide     (vi) ORIGINAL SOURCE:
        (A) ORGANISM: solanum tuberosum     (xi) SEQUENCE DESCRIPTION: SEQ ID NO:8:

```
Ser Leu Leu Asn Ser Leu Ser Thr Glu Lys
1               5                   10
```

(2) INFORMATION FOR SEQ ID NO:9:

(i) SEQUENCE CHARACTERISTICS:
        (A) LENGTH: 11 amino acids
        (B) TYPE: amino acid
        (C) STRANDEDNESS:
        (D) TOPOLOGY: linear     (ii) MOLECULE TYPE: peptide     (vi) ORIGINAL SOURCE:
        (A) ORGANISM: solanum tuberosum     (xi) SEQUENCE DESCRIPTION: SEQ ID NO:9:

```
Ala Asn Val Glu Arg Met Leu Thr Val Ser Lys
1               5                   10
```

(2) INFORMATION FOR SEQ ID NO:10:

(i) SEQUENCE CHARACTERISTICS:
        (A) LENGTH: 15 amino acids
        (B) TYPE: amino acid
        (C) STRANDEDNESS:
        (D) TOPOLOGY: linear     (ii) MOLECULE TYPE: peptide     (vi) ORIGINAL SOURCE:
        (A) ORGANISM: solanum tuberosum     (xi) SEQUENCE DESCRIPTION: SEQ ID NO:10:

```
Leu Glu Gln Thr Asn Tyr Gly Leu Pro Gln Gln Val Ile Glu Lys
1               5                   10                  15
```

(2) INFORMATION FOR SEQ ID NO:11:

```
        (i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (vi) ORIGINAL SOURCE:
            (A) ORGANISM: solanum tuberosum (xi) SEQUENCE DESCRIPTION: SEQ ID NO:11:

Tyr Gly Leu Pro Val Gln Val Phe Glu
1               5

(2) INFORMATION FOR SEQ ID NO:12:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide (vi) ORIGINAL SOURCE:
            (A) ORGANISM: solanum tuberosum (xi) SEQUENCE DESCRIPTION: SEQ ID NO:12:

Arg Thr Leu Leu Val Asn Leu Asn Ser Asp Asp Val Lys
1               5                   10
```

DEBRANCHING ENZYMES AND DNA SEQUENCES CODING THEM, SUITABLE FOR CHANGING THE DEGREE OF BRANCHING OF AMYLOPECTIN STARCH IN PLANTS

BACKGROUND OF THE INVENTION

The present invention relates to DNA sequences which on the codogenic strand, code plant debranching enzymes whose transcripts formed in transgenic plants code new proteins with the enzymatic activity of debranching enzymes which in transgenic plants reduce the degree of branching of amylopectin starch. (The invention also Relates) to DNA sequences which on the codogenic strand code plant debranching enzymes whose transcripts formed in transgenic plants prevent the synthesis of proteins with the enzymatic activity of debranching enzymes, which in transgenic plants increases the degree of branching of amylopectin starch, and also to recombinant plasmids on which these DNA sequences are localized and which can be introduced into plant cells and plants.

The invention also relates to a process for the production of plants changed by genetic engineering whose amylopectin starch is modified, and to the modified starch obtainable from these plants.

Polysaccharides such as starch are, alongside along with oils, fats and proteins, essential renewable raw materials from plants.

A decisive factor which stands in the way of the use of renewable raw materials is the lack of substances which precisely meet the requirements of the chemical industry in regard to form, structure, or other physico-chemical parameters. In order to make the application of renewable raw materials feasible in as many fields of use as possible, it is particularly important to achieve a great material diversity. In regard to polysaccharides, this means that, for example, as many different forms of starch must be provided as possible. This necessitates considering both strongly branched forms which are characterized by a high surface reactivity in their chemical properties, and mildly branched types which are distinguished by a high uniformity of structure. Uniformity of structure is an important prerequisite for highly efficient reaction control during chemical syntheses.

Although starch is a polymer comprising chemically uniform basic components, the glucose molecules, it is a complex mixture of very different molecule forms which differ in respect to their degree of polymerization and the occurrence of branchings of the glucose chains. Starch is therefore not a uniform raw material. In particular, a distinction is drawn between amylose starch, an essentially unbranched polymer comprising α-1,4 glycosidically linked glucose molecules, and amylopectin starch, which for its part is a complex mixture of differently branched glucose chains. The branchings come about through the occurrence of additional α-1,6 glycosidic linkages.

In typical plants for starch production, such, for example maize or potato, the two forms of starch occur in a ratio of roughly 25 parts amylose to 75 parts amylopectin.

In regard to the uniformity of a basic substance, such as starch, for its application in the industrial sector, plants are needed which, for example, contain only the component amylopectin or plants which contain only the component amylose. In regard to the versatility of the raw material starch, plants are needed which show forms of amylopectin with differently marked branching. There is thus a great interest in enzymes of the starch metabolism which can modify the degree of branching of the starch molecules, or in gene sequences which can be used for the genetically changing plants so as to be able to synthesize different forms of starch in plants.

It is already known that for certain plant species, for example maize, plant types which contain only amylopectin can be produced by mutagenesis in which individual genes of the plant are inactivated. For potato, a genotype which forms no amylose was likewise produced by chemical mutagenesis with a haploid line (Hovenkamp-Hermelink et al., 1987, Theor Appl Genet 75: 217–221). Haploid lines, or the homozygotic diploid or tetraploid lines developed from them, are not usable in agriculture, however. The mutagenesis technique is not applicable to the agriculturally interesting heterozygotically tetraploid lines, as an inactivation of all copies of a gene is technically not possible because of the presence of four different genotype copies. It is known from Visser et al. (1991, Mol Gen Genet 225: 289) that plant types which form substantially pure amylopectin starch can be produced by antisense inhibition of the gene for the starch granule-bound starch synthetase in potato.

A branching enzyme of the potato is known from WO 92/14827. This enzyme is known as the Q-enzyme of *Solanum tuberosum*. It is also known that, with the help of DNA sequences which contain the information for the branching enzyme of the potato described in WO 92/14827, transgenic plants can be produced in which the amylose/amylopectin ratio of the starch is changed.

While the occurrence of several Q-enzymes is known for other species, e.g. maize (Singh & Preiss, 1985, Plant Physiol 79: 34–40), it is not known whether, besides the branching enzyme of the potato known from WO 92/14827, other enzymes are involved in the synthesis of branched starch in potato. Besides the Q-enzymes which introduce branchings into starch molecules, enzymes occur in plants which dissolve branchings. These proteins, also known as debranching enzymes, are divided into three groups according to substrate specifity:

The pullulanases, which besides pullulane also use amylopectin, occur in microorganisms, e.g. Klebsiella, and plants. In plants, they are also called R-enzymes. The isoamylases, which do not work with pullulane, but do with glycogen and amylopectin, likewise occur in microorganisms and plants. An isoamylase of maize is described by Manners & Rowe (1969, Carbohydr. Res. 9: 107), and Ishizaki et al. (1983, Agric Biol Chem 47: 771–779) describe an isoamylase of potato. The amylo-1,6-glucosidases are described in mammals and yeasts and use limiting dextrins as substrates.

Besides five endo- and two exoamylases, Li et al. (1992, Plant Physiol 98: 1277–1284) detected only one debranching enzyme of the pullulanase type in sugar beet. This enzyme, which has a size of ca. 100 kDa and a pH optimum of 5.5, is localized in the chloroplast.

Ludwig et al. (1984, Plant Physiol 74: 856–861) describe a debranching enzyme from spinach which uses pullulane as a substrate but which displays an activity three times lower upon reaction with amylopectin.

In the case of the agriculturally important starch-storing cultivated plant the potato, the activity of a debranching enzyme was investigated in 1951 by Hobson et al. (1951, J Chem Soc 1451). It was demonstrated that the corresponding enzyme, unlike the Q-enzyme, does not possess a chain-extending activity and merely hydrolyses α-1,6 glycosidic bonds. However, it was possible neither to characterize the enzyme more precisely nor to describe DNA sequences which code a protein with the enzymatic activity of a debranching enzyme.

To date, no DNA sequences are known which code a protein with the enzymatic activity of a debranching enzyme from plants which, upon introduction into the plant genome, change the metabolism of the plant in such a way that the degree of branching of the amylopectin starch is increased or reduced.

SUMMARY OF THE INVENTION

The object of the present invention is to provide DNA sequences which code debranching enzymes on the codogenic strand, plasmids with which these DNA sequences can be introduced into plant cells or plants, plant cells from which whole plants can be regenerated and plants which make possible the production of amylopectin starch with an increased or reduced degree of branching.

There are now described the identification and purification of debranching enzymes and also peptide sequences of these enzymes and their use for the description of DNA sequences which in transgenic plants form transcripts which code proteins with the enzymatic activity of debranching enzymes, or which in transgenic plants form transcripts which prevent the synthesis of proteins with the enzymatic activity of debranching enzymes and plasmids and plant cells for the production of these transgenic plants.

Also described are transgenic plants which contain DNA sequences which code proteins with the enzymatic activity of debranching enzymes which reduce the degree of branching of amylopectin starch and transgenic plants which contain DNA sequences which prevent the synthesis of proteins with the enzymatic activity of debranching enzymes, which increases the degree of branching of amylopectin starch.

a) firstly, proteins with the activity of a debranching enzyme are purified to homogeneity (see example 1), b) peptide sequences are established from the purified enzyme by protein sequencing (see example 2), c) these peptide sequences are used for the cloning of cDNA sequences from a cDNA library, both immunological and molecular genetic methods being used (see examples 3 and 4) and/or d) these peptide sequences are used for the cloning of genomic DNA sequences from a genomic library with the help of molecular biological methods (example 5) and finally e) the DNA sequences from c) and/or d) are introduced into plasmids which make possible a transformation of plant cells and the regeneration of transgenic plants (see example 6).

The DNA sequences described by way of example in the examples with reference to the potato (*Solanum tuberosum*) code for a plant debranching enzyme which modifies the degree of branching of amylopectin starch naturally contained in plants in that the degree of branching of the amylopectin starch is increased or reduced as required. Protein sequences of debranching enzymes with at least one of the following sequences are coded from the codogenic DNA sequences:

```
Seq ID No. 1

Arg Thr Leu Leu Val Asn Leu Asp Ser Asp Val Lys Pro
    1               5                   10

Glu Gly Gly Asp Asn Leu Gln
    15              20

Seq ID No. 2

Arg Leu Ser Ser Ala Gly Ile Thr His Val His Leu Leu Pro
    1               5                   10

Thr Tyr Gln Phe Ala Gly
    15              20

Seq ID No. 3

Gly Ser Glu Val Leu Met His Asp Gly Lys
    1               5                   10

Seq ID No. 4

Ser Pro Ser Glu Ala Asp Pro Val Glu Ile Val Gln Leu Lys
    1               5                   10

Seq ID No. 5
    Asp Cys Ile Gln Val Gly Met Ala Ala Asn Asp Lys
    1               5                   10

Seq ID No. 6

Lys Leu Gln Leu His Pro Val Gln Met Asn
    1               5                   10

Seq ID No. 7

Glu Leu Asp Gly Val ValTrp Ser Ala Glu
    1               5                   10
```

-continued

```
Seq ID No. 8

Ser Leu Leu Asn Ser Leu Ser Thr Glu Lys
    1               5                   10

Seq ID No. 9

Ala Asn Val Glu Arg Met Leu Thr Val Ser Lys
    1               5                   10

Seq ID No. 10

Leu Glu Gln Thr Asn Tyr Gly Leu Pro Gln Gln Val Ile Glu
    1               5                   10

Lys
    15

Seq ID No. 11
    Tyr Gly Leu Pro Val Gln Val Phe Glu
    1               5 or Seq ID No. 12
    Arg Thr Leu Leu Val Asn Leu Asn Ser Asp Asp Val Lys
    1               5                   10
```

Transgenic plants with an increased or reduced degree of branching of amylopectin starch can be produced via a process which is characterized by the following steps:

a) Production of a DNA sequence with the following part-sequences:
  i) a promoter which is active in plants and ensures the formation of a RNA in proposed target tissues or target cells,
  ii) a DNA sequence which allows the transcription of RNA which, in transgenic plants, codes a new protein sequence with the enzymatic activity of a debranching enzyme or which allows the transcription of a RNA which in transgenic plants prevents the synthesis of a protein with the enzymatic activity of a debranching enzyme,
  iii) if necessary, a 3'-non-translated sequence which in plant cells leads to the ending of transcription and to the addition of poly-A radicals to the 3'-end of the RNA, b) transfer and incorporation of the DNA sequence into the genome of a plant cell, preferably using recombinant plasmids and c) regeneration of intact, whole plants from the transformed plant cells.

Preferably one, more or all of the protein sequences, Seq ID No. 1 to Seq ID No. 12, are contained in the protein sequence of the debranching enzyme named under ii). Recombinant plasmids according to process step b) contain the DNA sequences which on the codogenic strands code plant debranching enzymes or fragments thereof, whereby the transcripts derived from the DNA sequences in transgenic plants effect the synthesis of new proteins with the enzymatic activity of debranching enzymes which in the transgenic plants reduce the degree of branching of amylopectin starch or the transcripts derived from the DNA sequences in transgenic plants prevent the synthesis of endogenous proteins with the enzymatic activity of debranching enzymes, which in transgenic plants increases the degree of branching of amylopectin starch. The latter can be achieved through a cosuppression or by anti-sense RNA (Inouye, 1988, Gene 72: 25–34; Flavell, 1994, Proc. Natl. Acad. Sci. USA 91: 3490–3496).

The transgenic plants obtainable through the process with an increased or reduced degree of branching of amylopectin starch are also the subject of the invention. Plants to which the process is applied are useful plants such as e.g. maize, wheat and potato.

The invention also relates to proteins having the enzyme activity of a debranching enzyme, one or more of the sequences, seq ID No. 1 to Seq ID No. 12 and a molecular weight between 50 kd and 150 kd, especially between 70 kd and 130 kd, above all between 90 kd and 110 kd. The proteins are from plants, such as *Solanum tuberosum*.

For the identification of a new DNA sequence containing the information for the synthesis of a protein with the enzymatic activity of a debranching enzyme or for the suppression of the formation of an endogenous activity of a debranching enzyme, protein extracts were obtained from plants, (such as potato plant) by way of example. For the detection of the enzymatic activity of the debranching enzyme, as described in example 1, a colour test was used. When protein extracts of potato plants are separated in non-denaturing, amylopectin-containing polyacrylamide gels (PAAG), a protein with a starch-modifying activity can be detected by subsequent iodine dying. While unbranched amylose forms a blue-coloured complex with iodine, amylopectin produces a reddish-violet colouring. In amylopectin-containing PAAGs which turn reddish-violet with iodine, at places at which a debranching activity is localized, a colour shift to a blue colouring of the gel, occurs as the branchings of the violet-colouring amylopectin are broken down by the enzyme.

By separating the protein from others with the help of progressive ammonium sulphate precipitation and subsequent affinity chromatography at immobilized β-cyclodextrin, the protein is purified to homogeneity according to the invention. Peptide sequences are determined from the pure protein (see example 2). As a result, peptide sequences of a plant debranching enzyme are accessible for the first time. The peptide sequences of the debranching enzyme show, in individual areas, a certain homology to microbial debranching enzymes, but this is not true of all domains of the protein. The new debranching enzyme from *Solanum tuberosum* thus represents a previously unknown type of debranching enzymes.

The peptide sequences of the debranching enzyme serve according to the invention to identify DNA sequences in plants which code a peptide with the activity of a debranching enzyme. Immunological processes can be applied (see example 3) or molecular genetic methods are used (see examples 4 and 5).

After the DNA sequences which code a new debranching enzyme are identified, they can be multiplied in bacteria by cloning into vector plasmids. Examples of vectors are pBR322, pUC-series, m13mp-series etc. The DNA sequence which codes the new debranching enzyme can be provided with linkers which permit a simple recloning into other plasmids. For the purpose of introduction into plants (see example 6), binary plasmids which contain a replication signal, for example, for *Escherichia coli* and for *Agrobacterium tumefaciens* can be used preferably, but not exclusively. If these binary plasmids contain T-DNA elements, a transfer of the DNA sequence of a new debranching enzyme into the genome of dicotyledonous plants is particularly simple. Other methods are available however, for example transformation with the help of ballistic processes which are used for the transformation of monocotyledons (cf. Potrykus, 1991, Ann Rev Plant Mol Biol Plant Physiol 42: 205–225). To ensure an expression of the transferred transgene in genetically changed plants, the cDNA sequence of the new debranching enzyme is fused to a promoter sequence. All the promoters which are active in plants come into consideration in principle. Preferably promoters which are active in the starch-storing organs of the plants to be transformed a reused. Thus, in the case of maize, it is the maize granules, whereas in the case of the potato, it is the tubers.

The tuber-specific B33 promoter (Rocha-Sosa et al., 1989, EMBO J 8: 23–29) can be used in particular, but not exclusively, for the transformation of the potato. For the stabilization of the RNA formed by the transgene, a termination and polyadenylation signal is also appended if necessary to the DNA sequence coding the debranching enzyme. This can be, for example, the termination signal of the octopine synthase gene from *Agrobacterium tumefaciens*.

By fusing a promoter, a DNA sequence and, if necessary, a termination signal, constructs formed which are integrated into suitable plasmids for transformation of plants. These recombinant plasmids are also the subject of the present invention. The recombinant plasmids are used for the transformation of plant cells from which whole plants can be regenerated. These plant cells which contain the DNA sequences according to the invention are also the subject of the invention. The recombinant plasmids can also be used for the identification of nucleic acid sequences which code debranching enzymes.

As a result of the transfer of a DNA sequence which consists of promoter, coding region of a new debranching enzyme and termination/polyadenylation signal, a transgenic plant is produced in which RNA is formed which can serve as a matrix for the synthesis of a new debranching enzyme, or which, through interaction with an endogenous mRNA of a debranching enzyme, suppresses its synthesis. The type of RNA which is transcribed by the transgene depends on the orientation of the DNA sequence of the new debranching enzyme relative to the promoter. If the 5' end of the DNA sequence of the new debranching enzyme is fused to the 3' end of the promoter, a translatable mRNA is formed which serves as a matrix for the synthesis of a protein with the enzymatic activity of a new debranching enzyme. If, on the other hand, the 3' end of the DNA sequence of the new debranching enzyme is fused to the 3' end of the promoter, an antisense RNA forms which suppresses the translatability of the endogenous mRNA of the debranching enzyme.

In the first case, there is an additional enzymatic activity of a debranching enzyme in the plant. The result of this is that the degree of branching of the amylopectin formed by the transgenic plant is reduced. A starch thereby becomes accessible which, compared with the naturally occurring type, is distinguished by a more markedly ordered space structure and an increased uniformity, which has favourable consequences, for the film-formation properties in particular.

In the second case, an endogenous enzymatic activity of a debranching enzyme is suppressed. This leads to the formation of markedly branched starch in transgenic plants. Markedly branched amylopectin has a particularly large surface and is thereby suitable as copolymer to a particular extent. A marked degree of branching also leads to an improvement in the solubility of the amylopectin in water. This property is very favourable for certain technical applications. Potato is particularly suitable for the production of markedly branched amylopectin while exploiting the DNA sequences, according to the invention, of the new debranching enzyme, but the application of the invention is not limited to potato. The modified starch formed in the transgenic plants can be isolated from the plants or from the plant cells with commonly used methods and processed after purification for the production of foodstuffs and industrial products. The DNA sequences which code for a debranching enzyme can also be used for the isolation of homologous cDNA or of genomic sequences from other plant species, using standard methods.

DESCRIPTION OF THE FIGURES

In this.

| | |
|---|---|
| O = | protein extract of a homogenate of tuber tissue from *Solanum tuberosum*. |
| Passage = | passage through an affinity chromatography of the protein extract at immobilized β-cyclodextrin |
| β-cyclo dextrin = | elution of the affinity chromatography with dissolved β-cyclodextrin in the concentrations 1 mg/ml, and 10 mg/ml respectively. |
| DBE = | debranching enzyme from *Solanum tuberosum*. |
| DE = | Disproportionating enzyme from *Solanum tuberosum*. |

In this.

| | |
|---|---|
| A = | DraI/DraI fragment (position −1512 to +14) of the promoter region of the B33 gene of *Solanum tuberosum* (Rocha-Sosa et al., EMBO J 8:23–29), |
| B = | NotI/NotI fragment of cDNA with the coding region of the debranching enzyme of *Solanum tuberosum* in sense orientation to Fragment A. |
| C = | Polyadenylation signal of gene 3 of the T-DNA of the plasmid pTiACH5 (Gielen et al., EMBO J 3:835–846), nucleotides 11749 to 11939, which was isolated as PvuII/HindIII fragment from the plasmid pAGV40 (Herrera-Estrella et al., 1983, Nature 303: 209–213) and cloned after addition of a SphI linker to the PvuII cutting point between the SphI and the HindIII cutting points of the polylinker of pBIN 19. |

In this.

A = DraI/DraI fragment (position −1512 to +14) of the promoter region of the B33 gene of *Solanum tuberosum* (Rocha-Sosa et al., EMBO J 8:23–29),
B = NotI/NotI fragment of cDNA with the coding region of the debranching enzyme of *Solanum tuberosum* in anti-sense orientation to Fragment A.
C = Polyadenylation signal of gene 3 of the T-DNA of the plasmid pTiACH5 (Gielen et al., EMBO J 3:835–846), nucleotides 11749 to 11939, which was isolated as PvuII/HindIII fragment from the plasmid pAGV40 (Herrera-Estrella et al., 1983, Nature 303: 209–213) and cloned after addition of a SphI linker to the PvuII cutting point between the SphI and the HindIII cutting points of the polylinker of pBIN 19.

DETAILED DESCRIPTION OF THE INVENTION

Example 1
Identification of a New Debranching Enzyme in *Solanum tuberosum*

Figure 1:
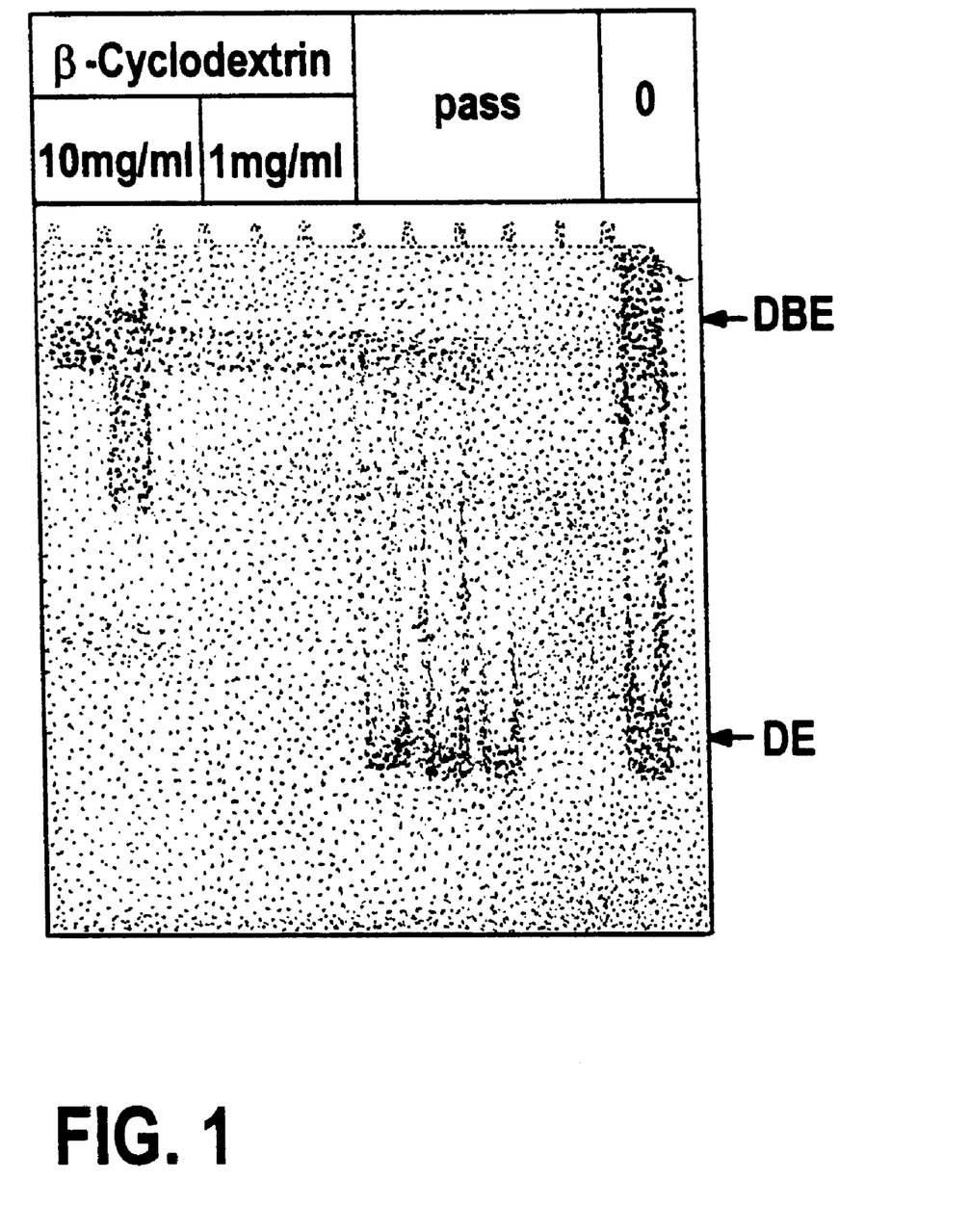
FIG. 1 shows the purification of the debranching enzyme from *Solanum tuberosum*.

Protein extracts of plants of the species *Solanum tuberosum* were obtained from tuber tissue. For this, 820 g tuber tissue are homogenized in 1500 ml of a buffer comprising 50 mM sodium acetate pH 6.0; 2.5 mM 1,4-dithio-DL-threitol; 1.5 mM mercaptoethanol; 0.4 mM PMSF and traces of sodium bisulphite, sodium sulphite and ascorbic acid (spatula tips in each case). 50 μl are separated from the homogenate (see trace 1 in FIG. 1) in a PAAG. The gel contains 7.5% acrylamide pH 8.6 which is crosslinked with methylene bisacrylamide up to a degree of 1:75, plus 1% amylopectin. The buffer system for the electrophoresis contains tris/glycine pH 8.9. After the gel run the gel is equilibrated in 50 mM tris/citrate pH 7.0; 2 mM ascorbic acid at 22° C. for 4 hours. The colouring of the gel takes place with Lugol's solution for 15 minutes. The result of the colouring is shown in FIG. 1, trace 1. Besides a red-coloured band, which goes back to the activity of an enzyme introducing branchings (branching enzyme or disproportionating enzyme), a strongly blue-coloured band is to be recognized. The blue colouring comes about through the enzymatic degradation of α-1,6 glycosidic branchings of the amylopectin which are responsible for its reddish or violet colour.

Example 2
Purification of a Debranching Enzyme from *Solanum tuberosum* and Determination of Peptide Sequences.

Ammonium sulphate is added, continuously at 4° C. with stirring up to a concentration of 40% of the saturation concentration, to a protein extract from tuber tissue of Solanum tuberosum obtained according to example 1. The partial precipitation of proteins which sets in is continued with stirring for two hours, then precipitated proteins are separated by centrifugation. Ammonium sulphate is added to the supernatant liquid, as described above, up to a value of 50% of the saturation concentration, proteins again being precipitated out. This protein fraction is separated by centrifugation and then fractionated further.

After dissolution of the precipitate in 20 ml acetate buffer (see example 1) and 12 hours' dialysis against double-distilled water, the protein solution is subjected to a chromatography. 500 mg protein from the fractionated ammonium sulphate precipitation are applied per 30 ml bed volume onto a Sepharose 6B column to which β-cyclodextrin was coupled. Washing with acetate buffer follows until the eluate displays no absorption at 280 nm. A protein fraction with low affinity to the stationary phase is then eluted with a β-cyclodextrin solution of 1 mg/ml acetate buffer, which is discarded. At a cyclodextrin concentration of 10 mg/ml acetate buffer, the debranching enzyme of potato is eluted (cf. FIG. 1, trace *)

The fraction of the eluate highly enriched with debranching enzyme is subjected to an electrophoresis in a denaturing PAAG in accordance with Laemmli's instructions (1970, Nature 227: 680–685). The now denatured protein is cut out from the gel. Peptide sequences are determined by standard procedures.

The peptide sequences of the debranching enzyme from *Solanum tuberosum* are reproduced in Seq-ID No. 1 to Seq-ID No. 12.

Example 3
Isolation of cDNA Sequences which Code a Debranching Enzyme of *Solanum tuberosum*, with the Help of Immunological Methods The protein purified according to example 2 is used for she immunization of rabbits. With the help of the serums of immunized rabbits, cDNA libraries which are representative of transcripts of the tuber tissue of *Solanum tuberosum* are screened for cDNA clones which contain sequences which code for the debranching enzyme of *Solanum tuberosum*. For this, total RNA is prepared from tuber tissue of *Solanum tuberosum* according to Logemann et al. (1987, Anal Biochem 163: 16–20). mRNA, polyadenylated by standard methods, is prepared from the total RNA, and used according to the procedure described by Gubler & Hoffmann (1983, Gene 25: 263) for the synthesis of cDNA. The cDNA is ligated with commercial EcoRI/NotI adapters and then ligated into the EcoRI cutting point of the expression system lambda ZAPII. After packing of the lambda phage DNA into phage heads, *E. coli* cells of the strain XL1-Blue are infected and plated out on medium in Petri dishes in a density of 25,000 per ca. 75 cm². After ca. 3 hours' incubation, nitrocellulose filters steeped in 10 mM IPTG solution are laid on the lysated bacteria cultures, and removed after another 3 hours. The filters are used for an immunological sounding by the Western blot technique described in example 5. pBluescript plasmids are obtained by in-vivo excision from the phage species obtained after three sounding cycles which contain the cDNA sequence of the debranching enzyme of *Solanum tuberosum*. The sequence of the cDNA is determined using the method of Sanger et al. (1977, Proc Natl Acad Sci USA 74: 5463–5467). The insertion can be isolated by cutting with corresponding restriction enzymes from the pBluescript plasmid which contains the sequence of the debranching enzyme of *Solanum tuberosum* and cloned by standard procedures into binary plasmids with the aim of transforming plants (see example 6).

Example 4
Isolation of cDNA Sequences which Code a Debranching Enzyme of *Solanum tuberosum*, with the Help of Molecular Genetic Methods The peptide sequences obtained according to example 2 are used for the derivation of oligonucleotide sequences which, taking account of the degeneracy of the genetic code, reproduce extracts of the DNA sequence of the debranching enzyme of *Solanum tuberosum*. According to the derived oligonucleotide sequences, synthetic oligonucleotides are synthesized by standard methods. These are used for the scrutiny of cDNA libraries which are representative for transcripts of the tuber tissue of *Solanum tuberosum*. Firstly, a cDNA library is produced by preparing total RNA from tuber tissue of *Solanum tuberosum* according to Logemann et al. (1987, Anal Biochem 163: 16–20). mRNA, polyadenylated by standard methods, is prepared from the total RNA, and used according to the procedure described by Gubler & Hoffmann (1983, Gene 25: 263) for the synthesis of cDNA. The cDNA is ligated with commercial EcoRI/NotI adapters and then ligated into the EcoRI cutting point of the DNA of the phage lambda ZAP II. After packing of the lambda phage DNA into phage heads, *E. coli* cells of the strain XL1-Blue are infected and plated out on medium in Petri dishes in a density of 25,000 per ca. 75 cm². After ca.9 hours' incubation, nylon membranes are laid on the lysated bacteria cultures, and removed after 1 minute. The filters are incubated for 1 minute in 250 mM HCl, for 5 minutes in 0.5 M NaOH; 1.5 M NaCl, then for 5 minutes in 1 M tris/HCl pH 7.5. After drying and fixing at 80° C. for 1 hour, the filters are incubated for 4 hours in a buffer comprising 2 fold SSC (sodium chloride/sodium citrate)

10 fold Denhardt's solution 0.1% SDS (sodium dodecyl sulphate)

5 mM EDTA (ethylene diamine tetraacetic acid)

50 mM di-sodium phosphate

250 µg/ml herring sperm DNA

50 µg/ml tRNA before the radioactively terminally labelled oligonucleotides are added. After 12 hours' hybridization, the filters are washed in 2 fold SSC/0.5% SDS and then autoradiographed. The temperature for hybridization and washing of the filters is calculated as follows:

$$T+15=16.6\times[Na+]+0.41\times\%GC_{OLIGONUCLEOTIDE}+81.5-675/\text{length}_{OLIGONUCLEOTIDE}$$

Suitable oligonucleotide sequences can be calculated from the peptide sequences reproduced in Seq-ID No 1 or Seq-ID No 2 of the debranching enzyme of *Solanum tuberosum*. In order to obtain the highest possible hybridization temperature which guarantees an adequate specifity of the hybrid formation, the longest possible oligonucleotides are to be used. But as the length increases, so does the degree of degeneracy, i.e. the number of oligonucleotides with different sequence combinations. Degrees of degeneracy of up to 6000 can be accepted. For the peptide sequence given in Seq-ID No 1, the sequence for an oligonucleotide probe of length 26 bp was derived. The oligonucleotide has a degree of degeneracy of 3072 at a GC content of 61% maximum and 38% minimum. This gives a maximum hybridization temperature of 56° C. The basic sequence for the synthesis of the probe reads:

Natl Acad Sci 74: 5463–5467). The cDNA is isolated by standard methods (Sambrook et al., 1989, Molecular cloning: a laboratory manual, 2nd Ed., Cold Spring Harbor Laboratory Press, NY USA) from the pBluescript derivative after digestion with ECORI or NotI and can be cloned by standard methods into binary plasmids with the aim of the transformation of plants (see example 6).

Example 5

Isolation of Genomic DNA Sequences which Code a Debranching Enzyme of *Solanum tuberosum*, with the Help of Molecular Genetic Methods.

The peptide sequences obtained according to example 2 are used for the derivation of oligonucleotide sequences which, taking account of the degeneracy of the genetic code, reproduce extracts of the DNA sequence of the debranching enzyme of *Solanum tuberosum*. According to the derived oligonucleotide sequences, synthetic oligonucleotides are synthesized by standard methods. These are used for the scrutiny of genomic DNA libraries which represent the genome of *Solanum tuberosum*.

Firstly, a genomic DNA library is produced according to Liu et al. (1991, Plant Mol Biol 17: 1139–1154). *E. coli* cells of the strain P 2392 are then infected with the phages containing the genomic DNA fragments and plated out on medium in Petri dishes in a density of 30,000 per cm². After ca. 8 hours' incubation, nitrocellulose membranes are laid onto the lysated bacterial lawn, which are removed after a minute. The filters are incubated for 2 minutes in 0.2 M NaOH, 1.5 M NaCl; 2 minutes in 0.4 M tris/HCl pH 7.5, then for 2 minutes in 2 fold SSC. After drying, the fixing of the DNA takes place via UV crosslinking. The filters are then incubated for 3 hours in a buffer comprising 2 fold SSC (sodium chloride/sodium citrate)

10 fold Denhardt's solution 0.15% SDS (sodium dodecyl sulphate)

5 mM EDTA (ethylene diamine tetraacetic acid)

50 mM di-sodium phosphate 250 mg/ml herring sperm-DNA before the radioactively terminally labelled oligonucleotides are added. After 12 hours' hybridization, the filters are washed in 0.2 fold SSC/0.1% SDS and then autoradiographed. The temperature for hybridization and washing of the filters is calculated as follows:

$$16.6\times[Na^+]+0.41\times[\%GC_{oligonucleotide}]+81.5-675/\text{length}_{oligonucleotide}-15=T$$

Suitable oligonucleotide sequences can be calculated from the peptide sequences, reproduced in Seq-ID No 1 or

```
Peptide Seq-ID No. 1:  Asp Ser Asp Asp Val Lys Pra Glu Gly
              mRNA: 5' GAU UCN GAU GAU GUN AAA CCN GAA GG 3'
                         C AG   C   C       G       G
              probe: 3' CTA AGN CTA CTA CAN TTT GGN CTT CC 5'
                         G TC   G   G       C       C
```

In three probing cycles, phage species which contain the cDNA sequence of the debranching enzyme of *Solanum tuberosum* are isolated and used for the in-vivo excision of a pBluescript plasmid by standard methods. As insertion of a pBluescript plasmid, the sequence of the cDNA is determined according to the method of Sanger et al. (1977, Proc Seq-ID No 6, of the debranching enzyme of *Solanum tuberosum*. In order to obtain as high as possible a hybridization temperature which guarantees an adequate specifity of the hybridization, the longest possible oligonucleotides are to be used. However, as the length increases, so does the degree of degeneracy, i.e. the number of oligonucleotides with different sequence combinations. Degrees of degeneracy of up to 10 000 can be accepted. If several peptide sequences from a protein are known, oligonucleotides can be calculated accordingly and used jointly in an oligonucleotide mixture for hybrid formation. This can increase the efficiency of the hybrid formation. For the peptide sequence given in Seq ID No. 1, the sequence for an oligonucleotide probe of length 26 bp was derived. The oligonucleotide has a degree of degeneracy of 3072 at a GC content of 61% maximum and 38% minimum. This gives a maximum hybridization temperature of 56° C. For the peptide sequence given in Seq ID No 6, the sequence for an oligonucleotide probe of length 20 bp was derived. The oligonucleotide has a degree of degeneracy of 384 at a GC content of 55% maximum and 50% minimum. The maximum hybridization temperature to be calculated from this is 60° C. Both oligonucleotide probes are used as a mixture at a temperature of 54° C. for hybridization.

The basic sequence for the synthesis of the probes reads:

```
Peptide Seq ID No. 1: Asp Ser Asp Asp Val Lys Pro Glu Gly
       mRNA: 5' GAU UCN GAU GAU CUN AAA CCN GAA GG 3'
                    C AG    C   C       G       G
      probe: 3' CTA AGN CTA CTA CAN TTT GGN CTT CC 5'
                    G TC    G   G       C       C Peptide Seq ID No. 6: Ile Gln Val Gly Met Ala Ala
       mRNA: 5' AUU CAA GU—GG—AUG GC—GC    3'
                    C   G
                    A
      probe: 3' TAA GTT CAI CCI TAC CGI CG   5'
                    G   C
                    T
```

In three probing cycles, phage species which contain the genomic DNA sequence of the debranching enzyme of *Solanum tuberosum* are isolated. The genomic DNA insertions are isolated from positive clones by suitable restriction enzymes and separated by gel electrophoresis. The lambda DNA is separated from the genomic DNA sequence and then isolated by standard methods (Sambrook et al., 1989, Molecular cloning: a laboratory manual, 2nd Edition, Cold Spring Harbor Laboratory Press, NY USA), cloned into a pBluescript plasmid and transformed in *E coli* cells of the strain DH5-α. As the genomic DNA produced according to example 5 has a length 8 kb to 15 kb on an average, subfragments with a length of 500 bp to 3.5 kb are produced using standard methods by means of suitable restriction enzymes and subcloned into pBluescript plasmids. The sequence of the inserted DNA of the different pBluescript plasmids is determined using the method of Sanger et al. (1977, Proc Natl Acad Sci USA, 74: 5463–5467).

The sequences which code a debranching enzyme of *Solanum tuberosum* are isolated after restriction digestion with suitable enzymes and can be cloned by standard methods into binary plasmids with the aim of the transformation of plants (see example 6).

Example 6

Figure 2:
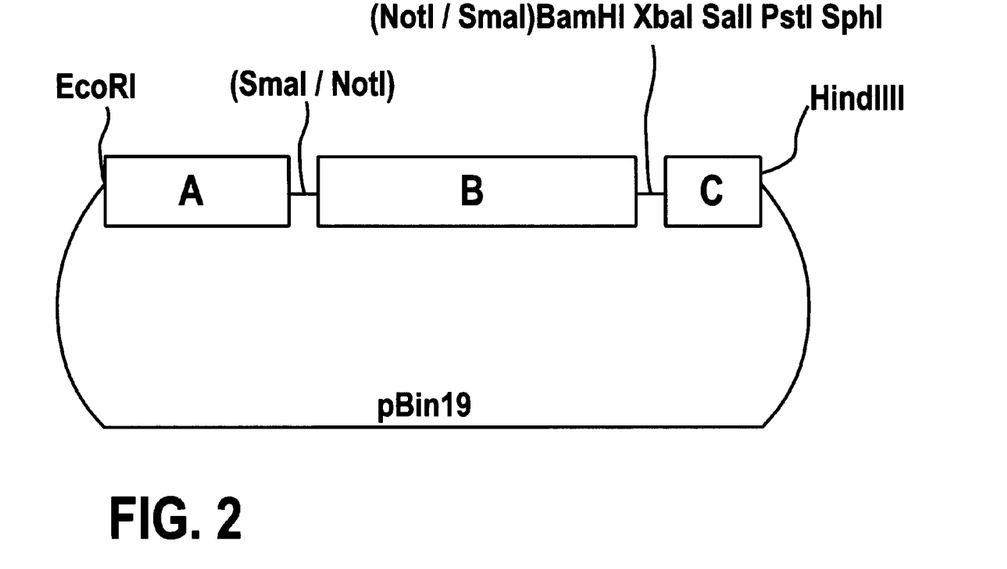
FIG. 2 shows the plasmid pB33-R, which is a derivative of the plasmid pBIN19 (Bevan, M., 1984, Nucl Acids Res 12: 8711–8721).
Figure 3:
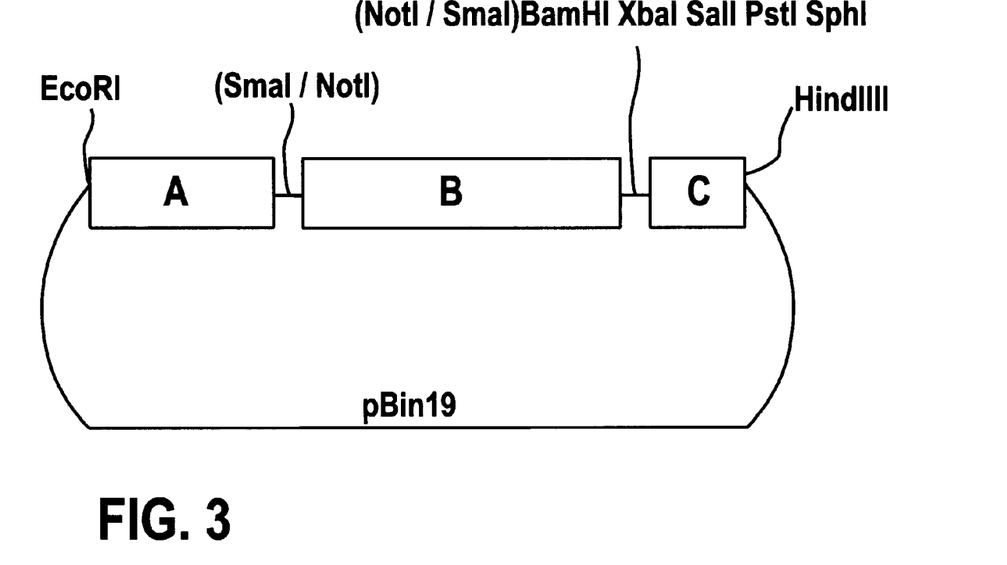
FIG. 3 shows the plasmid pB33-R-anti, which is a derivative of the plasmid pBIN19 (Bevan, M., 1984, Nucl Acids Res 12: 8711–8721).

Construction of Binary Plasmids for the Transformation of *Aarobacterium tumefaciens* and for the genetic modification of plants with the help of Agrobacterium For the plant transformation, the cDNA which was obtained according to example 3 or 4 as insertion in pBluescript was recloned into a binary vector which is derived from pBIN19 (Bevan (1984) Nucl Acids Res 12: 8711–8720). Two structures were produced: on the one hand, the plasmid pB33-R, and on the other, the plasmid pB33-R-anti (cf. FIG. 2 and FIG. 3). The two constructs contain, as promoter for the expression of a transgene in plants, the B33 promoter of *Solanum tuberosum* (Rocha-Sosa et al., EMBO J 8: 23–29). Whereas pB33-R contains the cDNA in sense orientation, i.e. leads to the formation of a translatable RNA in transgenic plants, pB33-R-anti represents an antisense structure for the inhibition of the expression of the endogenous gene. The constructs were produced as follows:

pB33-R: the promoter of the B33 gene of *Solanum tuberosum* was cloned as DraI fragment (position −1512 to +14 according to Rocha-Sosa et al., EMBO J8: 23–39) after degradation of overhanging ends with polymerase II into the SacI cutting point of the plasmid pUC19. An EcoRI/SmaI fragment, the promoter region was cloned into the binary vector pBIN19 which contains the termination signal of the octopine synthase gene from *Agrobacterium tumefaciens* in direct proximity to a polylinker comprising M13mp19. pB33 was formed in the process. The filled NotI fragment of the cDNA isolated according to example 3 or 4 was cloned into the SmaI cutting point of pB33 in sense orientation relative to the promoter (5' end of the cDNA against the 3' end of the promoter). pB33-R was formed in the process.

pB33-R-anti: the filled NotI fragment of the cDNA according to example 3 or 4 was cloned into the binary vector pB33 in antisense orientation relative to the promoter (3' end of the cDNA against the 3' end of the promoter). pB33-R-anti was formed in the process.

Corresponding to the constructs pB33-R and pB33-R-anti, plasmids were constructed which, instead of the cDNA, contain a genomic DNA sequence which codes for a debranching enzyme from *Solanum tuberosum*. For this, the coding DNA sequences were isolated from the pBluescript plasmids obtained according to example 5 with the help of suitable restriction endonucleases, the overhanging ends were filled and the obtained DNA fragments cloned into the SmaI cutting point of pB33 in sense or antisense orientation.

For the transformation of *Agrobacterium tumefaciens*, the binary plasmid is introduced into the cells by direct transformation according to the Höfgen & Willmitzer method (1988, Nucl Acids Res 16: 9877). The plasmid DNA of transformed agrobacteria were isolated according to the method of Birnboim et al. (1979) Nucl Acids Res 7: 1513–1523 and analysed by means of gel electrophoresis after suitable restriction cleavage. For the transformation e.g. of potato plants, 10 small leaves, scarified with a scalpel, of a sterile culture are for example laid in 10 ml MS medium with 2% sucrose which contains 30–50 μl of an *Agrobacterium tumefaciens* overnight culture grown under selection. After 3–5 minutes' light shaking, the Petri dishes are incubated at 25° C. in the dark. After 2 days, the leaves are laid out on MS medium with 1.6% glucose, 2 mg/l zeatin ribose, 0.02 mg/l naphthyl acetic acid, 0.02 mg/l gibberellic acid, 500 mg/l Claforan, 50 mg/l kanamycin and 0.8% bacto-agar. After one week's incubation at 25° C. and 3000 lux, the Claforan concentration in the medium is reduced by half. Further cultivation took place as described by Rocha-Sosa et al. (1989) EMBO J I 8: 29.

The testing of the success of the genetic modification of the plants is possible through analysis of the total RNA as regards the occurrence of a mRNA which codes the debranching enzyme (in the case of the transformation with pB33-R), or as regards the disappearance of the endogenous mRNA in the case of transformation with pB33-R-anti. The isolation of plant total RNA takes place according to Logemann et al. (1987) Anal Biochem 163: 16–20. For the analysis, 50 µg each total RNA are checked, with the help of Northern blots, for the presence or absence of the transcript.

To test for the presence of the debranching enzyme in transgenic plants, there is an extraction of total protein from plant tissue and then a Western blot analysis with the antiserum from rabbits described in example 3. For this, protein extracts are separated by means of gel electrophoresis in SDS-PAAG according to molecular weight. After SDS PAAG electrophoresis (PAGE), protein gels are equilibrated for 15–30 minutes in transfer buffer for graphite electrodes (48 g/l tris, 39 g/l glycine, 0.0375% SDS, 20% methanol) and then transferred at 4° C. onto nitrocellulose filter with 1.3 mA/cm$^2$ for 1–2 hours. The filter is saturated for 30 minutes with 3% gelatine in TBS buffer (20 mM tris/HCl pH 7.5; 500 mM NaCl). The filter is then incubated for 2 hours with the antiserum in suitable dilution (1: 1000–10,000 in TBS buffer) at room temperature. The filter is then washed for 15 minutes each with TBS, TTBS (TBS buffer with 0.1% polyoxyethylene-(20)-sorbitan monolaurate) and TBS buffer. After the washing, the filter is incubated for 1 hour at room temperature with alkaline phosphatase-conjugated goat-anti-rabbit (GAR) antibodies (1: 7,500 in TBS). The filter is then washed as described above and equilibrated in AP buffer (100 mM tris/HCl pH 9.5, 100 mM NaCl, 5 mM MgCl$_2$). The alkaline phosphatase reaction is started by substrate addition of 70 µl 4-nitrotetrazolium (NBT) solution (50 mg/ml NBT in 70% dimethylformamide) and 35 µl 5-bromo-4-chloro-3-indolyl phosphate (BCIP) (50 mg/ml BCIP in dimethylformamide) in 50 ml AP buffer. After 5 minutes, first signals can be observed as a rule. For the determination of the amylose/amylopectin content in the starch of transgenic potato plants, small leaf pieces with a diameter of 10 mm are floated for 14 hours under continuous light on 6% sucrose solution. A markedly increased starch formation in the small leaf pieces is induced by this light incubation. After the incubation, the amylose and amylopectin concentration is determined according to Hovenkamp-Hermelink et al. (1988, Potato Research 31: 241–246). The determination of the degree of branching (α-1,6 glycosidic bonds), of the chain length and of the size of the starch granules takes place according to Morrison et al. (1990, Methods in Plant Biochemistry Academic Press Lmtd. 2: 323–352).

What is claimed:

1. An isolated DNA sequence as contained in plasmid pB33-R or plasmid pB33-R-anti from potato, wheat or maize, said sequence coding for a plant debranching enzyme on the codogenic strand, wherein the transcripts formed by the sequence in a transgenic plant code for a protein having enzymatic activity of debranching enzymes which reduce the degree of branching of amylopectin starch in the transgenic plant.

2. An isolated DNA sequence as contained in plasmid pB33-R or pB33-R anti from potato, wheat or maize, said sequence coding for a plant debranching enzyme on the codogenic strand wherein the transcripts formed by the sequence in a transgenic plant prevent the synthesis of proteins having enzymatic activity of debranching enzymes, which increases the degree of branching of amylopectin starch in the transgenic plant.

3. An isolated DNA sequence as contained in plasmid pB833-R or pB33-R anti encoding a protein sequence selected from the group consisting of SEQ ID No. 1 to SEQ ID No. 12.

4. A recombinant plasmid pB33-R or pB33-R-anti comprising at least one DNA sequence from potato, wheat or maize, said sequence coding a plant debranching enzyme or fragment thereof on a codogenic strand, wherein the transcripts derived from the DNA sequence in a transgenic plant effect the synthesis of proteins with the enzymatic activity of debranching enzymes which in said transgenic plant reduce the degree of branching of amylopectin starch.

5. A recombinant plasmid pB33-R or pB33-R-anti comprising at least one DNA sequence from potato, wheat or maize, said sequence encoding a plant debranching enzyme or fragment thereof on the codogenic strand, wherein the transcripts derived from the DNA sequence in a transgenic plant prevents the synthesis of endogenous proteins with the enzymatic activity of debranching enzymes, which in said transgenic plant increases the degree of branching of amylopectin starch.

6. A recombinant plasmid according to claim 4 wherein said DNA sequence encodes at least one of the protein sequences selected from the group consisting of SEQ ID No. 1 to SEQ ID No. 12.

7. A plant cell comprising at least one DNA sequence from potato, wheat or maize according to claim 1.

8. An isolated DNA sequence as contained in plasmid pB33-R or plasmid pB33-R-anti from potato, wheat or maize encoding a plant debranching enzyme wherein a transcript formed by the DNA sequence in a transgenic plant codes for a protein having enzymatic activity of a debranching enzyme which reduces or increases the degree of branching of amylopectin starch in the transgenic plant.

9. A method for producing a recombinant protein having the enzymatic activity of a debranching enzyme, one or more of the peptide sequences SEQ ID No. 1 to SEQ ID No. 12, and a molecular weight between 50 kd and 150 kd which comprises expressing the isolated DNA sequence as claimed in claim 1 in a cell and subsequently isolating the recombinant protein from the cell.

10. The method for producing a recombinant protein as claimed in claim 9, wherein the molecular weight is between 70 kd and 130 kd.

11. The method for producing a recombinant protein as claimed in claim 9, wherein the molecular weight is between 90 kd and 110 kd.

12. The method for producing a recombinant protein as claimed in claim 9, wherein the recombinant protein is from a potato, wheat or maize plant.

13. The method for producing a recombinant protein as claimed in claim 9, wherein the recombinant protein is from *Solanum tuberosum*.

14. An isolated DNA sequence from potato, wheat or maize encoding a plant debranching enzyme wherein the DNA sequence hybridizes to the DNA encoding the enzyme in plasmid pB33-R and wherein a transcript formed by the DNA sequence in a transgenic plant codes for a protein having enzymatic activity of a debranching enzyme which reduces or increases the degree of debranching of amylopectin starch in the transgenic plant.

15. An isolated DNA sequence from potato, wheat or maize encoding a plant debranching enzyme wherein the DNA sequence hybridizes to the DNA encoding the enzyme in plasmid pB33-R-anti and wherein a transcript formed by the DNA sequence in a transgenic plant codes for a protein having enzymatic activity of a debranching enzyme which reduces or increases the degree of debranching of amylopectin starch in the transgenic plant.

16. The isolated DNA sequence of claim 14 wherein a transcript formed by the DNA sequence in a transgenic plant codes for a protein having the amino acid sequences of SEQ ID No. 1 and SEQ ID No. 12 and the enzymatic activity of a debranching enzyme which reduces or increases the degree of branching of amylopectin starch in the transgenic plant.

17. The isolated DNA sequence of claim 15 wherein a transcript formed by the DNA sequence in a transgenic plant codes for a protein having the amino acid sequences of SEQ ID No. 1 and SEQ ID No. 12 and the enzymatic activity of a debranching enzyme which reduces or increases the degree of branching of amylopectin starch in the transgenic plant.

* * * * *